US00PP27074P2

(12) United States Plant Patent
Trucks

(10) Patent No.: US PP27,074 P2
(45) Date of Patent: Aug. 16, 2016

(54) ***MISCANTHUS* PLANT NAMED 'OKTOBERFEST'**

(50) Latin Name: *Miscanthus sinensis*
Varietal Denomination: Oktoberfest

(71) Applicant: Gary M. Trucks, Benton Harbor, MI (US)

(72) Inventor: Gary M. Trucks, Benton Harbor, MI (US)

( * ) Notice: Subject to any disclaimer, the term of this patent is extended or adjusted under 35 U.S.C. 154(b) by 79 days.

(21) Appl. No.: 14/544,384

(22) Filed: Dec. 31, 2014

(51) Int. Cl.
*A01H 5/12* (2006.01)

(52) U.S. Cl.
USPC ..... Plt./384

(58) Field of Classification Search
USPC ..... Plt./384
See application file for complete search history.

*Primary Examiner* — Annette Para

(57) ABSTRACT

A new and distinct cultivar of ornamental *Miscanthus sinensis* plant named 'Oktoberfest' early blooming dark red-purple flowers on large showy spikes. The short wide foliage develops a deep purple-red color later in the summer that holds the color well into fall. The habit is narrow with upright foliage that begins arching toward the middle of the length.

1 Drawing Sheet

Botanical classification: *Miscanthus sinensis.*
Variety denomination: 'Oktoberfest'.

BACKGROUND AND CROSS REFERENCE TO RELATED PLANTS

*Miscanthus sinensis* 'Oktoberfest', hereinafter also referred to as 'Oktoberfest' and the "new plant" is a new and distinct cultivar of maiden grass. It was from open pollinated seed collected by Gary M. Trucks in fall of 2008 from *Miscanthus* 'Malepartus' (not patented) at a nursery in Benton Harbor, Mich., USA. The male parent is unknown, but may have been one of several in the breeding area as *Miscanthus* are generally considered self-sterile and pollen is windborne. The seeds were planted in spring of 2009 at the same nursery in Benton Harbor, Mich. with the first evaluations conducted the fall of 2009. Final evaluation and approval for introduction of the single seedling was done at a wholesale perennial nursery in Zeeland, Mich., USA in summer and fall of 2011.

Compared to the female parent, *Miscanthus* 'Malepartus', the new plant has shorter and wider foliage, colors up earlier with purple-red and is held more upright producing a more narrow upright plant habit. *Miscanthus* 'Oktoberfest' also has improved flowering with earlier coloring blooms that turn and hold onto their deep red-purple that holds through late fall frosts.

The nearest comparison cultivar known to the inventor is *Miscanthus* 'Huron Sunrise' (not patented). Compared to 'Huron Sunrise', the new plant has wider and shorter foliage with a white midrib. 'Oktoberfest' also is shorter in plant habit and blooms earlier with larger flower spikes that have a darker red-purple color. The leaves of 'Oktoberfest' develop a deep purple-red fall color earlier than 'Huron Sunrise' and retain their coloration for a longer period.

The new plant has been successfully asexually propagated by division at the same perennial plant nursery in Benton Harbor, Mich. since 2010, as well as plant tissue culture at a nursery in Zeeland, Mich., and found to produce stable and identical plants that maintain the unique true-to-type characteristics of the original plant in successive generations of asexual reproduction.

SUMMARY AND GENERAL DESCRIPTION OF THE PLANT

*Miscanthus* 'Oktoberfest' differs from its parents as well as all other *Miscanthus* known to the applicant in the following combined characteristics:

1. Early blooming dark red-purple flowers on large showy spikes.
2. Foliage that develops deep purple-red color later in summer and holds the color well into fall.
3. Short, wide leaves with white midrib.
4. Narrow habit.

BRIEF DESCRIPTION OF THE DRAWINGS

The photograph of the new plant demonstrate the overall appearance of the plant, including the unique traits. The colors are as accurate as reasonably possible with color reproductions. Ambient light spectrum, intensity, source and direction may cause the appearance of minor variation in color. The plant in the photograph is a three-year old plant grown in full-sun trial garden in Zeeland, Mich., USA.

The FIGURE shows the overall plant in mid-season.

DETAILED BOTANICAL DESCRIPTION

The following descriptions and color references are based on the 2001 edition of The Royal Horticultural Society Colour Chart except where common dictionary terms are used. *Miscanthus* 'Oktoberfest' has not been observed under all possible environments. The phenotype may vary slightly with different environmental conditions, such as temperature, light, fertility, moisture and maturity levels, but without any change in the genotype. The following observations and size descriptions are of a three-year old plant in a trail garden in Zeeland, Mich. in full sun with supplemental water and fertilizer.

Female or seed parentage: *Miscanthus sinensis* 'Malepartus' (not patented).

Male or pollen parent: Unknown.

Propagation method: By division of the culms and by shoot tissue culture, preferably in spring.

*Time to finishing in a three-liter pot*.—Three months.

Rooting habit: Normal, coarse, branching; root color cream to light tan depending on soil type.

Plant description: Hardy herbaceous perennial forming tightly rhizomatous clump, with upright culms and arching leaves producing a medium landscape texture.

*Plant size*.—Foliage height before flowering is about 132 cm tall from soil line to the top of the leaves, about 50 cm wide at soil line, about 145 cm at widest point just below flowers and about 170 cm tall to top of flowers.

Foliage description: Glaucous, glabrous, entire except microscopically serrulate, conduplicate toward culm along center vein and flattening toward middle and apex, alternate, mostly erect to arching toward tips and outer most leaves, sheathed from node of attachment to ligule, linear, deciduous but persist through winter.

*Leaf size*.—To about 84 cm long and about 12.0 mm wide; averaging 70 cm long and 10.0 mm wide.

*Leaf color*.—Young expanding leaves abaxial surface between RHS 138B and RHS 138C and adaxial surface nearest RHS 138A; midseason abaxial RHS N138A on top and RHS 138A underneath; late summer and fall leaves abaxial surface between RHS N187C and RHS 187C; late summer and fall adaxial leaves range from between RHS N187A and RHS N187B in the early phase to between RHS 186C and RHS N187C, nearest RHS N172B, between RHS N172 C and RHS 171D and between RHS 179B and RHS 179C in the fall with abaxial surfaces more gray than adaxial phase; both surfaces winter foliage develop to lighter than RHS 199D and more gray than RHS 164D.

*Color at ligule*.—Nearest RHS 165D on lower leaves and between RHS N187A and RHS N187C in upper leaves.

Veins: Parallel, center vein about 2.0 mm wide, ridged below and impressed above; Secondary vein color: secondary veins same as the surrounding leaf on both the abaxial and adaxial surfaces as leaf goes through seasonal phase changes.

*Center vein color*.—And between RHS 155D and RHS 193D through mid-season; variably changing with seasons to between RHS 186C and RHS 186D, nearest RHS 186D along with lighter than RHS 168D.

*Culm*.—Erect, cylindrical, completely enclosed by leaf sheath; about 60 per plant; to about 115 cm long, average about 152 cm without panicle, about 8.0 mm wide at base; internode length 5 to 8 cm.

*Ligule*.—Fringed membranous with fine hairs to 5 mm long; hair color RHS 165D.

Flower description: Rachis, one rachis per culm, beginning mid-September, drying on plants but persisting through winter; no fragrance detected.

*Rachis*.—Basally fan-branched, 35 to 40 cm long, 30 to 32 cm wide at widest portion; about 30 branches to about 26.5 cm long.

*Rachis color*.—Beginning nearest RHS 187B and developing to RHS 161 C when mature.

*Rachilla*.—Less than 1.0 mm long; color nearest RHS 161D when mature.

*Spikelet*.—Paired, with several long awns.

*Awns*.—To about 7.5 mm long; color silvery white lighter than RHS 155D to between RHS 185B and RHS 185C.

*Glumes*.—Lower to about 5.0 mm long and less than 1.0 mm wide; color between RHS 185B and RHS 185C.

Gynoecium: Stigma: two, plumose, protruding about 2.5 mm from glume; color between RHS 187A and RHS 187C.

Androecium: Filaments: fine, hair-like, white, less than 1 mm diameter and up to 2.0 mm long; Anther: oblong, basifixed, longitudinal; about 2.5 mm long and about 0.8 mm across; color nearest RHS 187 B.

Fruit: Caryopsis; about 2.5 mm long and about 1.5 mm wide; color nearest RHS 164C.

Hardiness: The plant grows best with plenty of moisture and adequate drainage, but is able to tolerate some drought when mature. Hardiness at least from USDA zone 5 through 9.

Pest and disease resistance: Disease and pest resistance beyond what is typical of that of other maiden grasses has not been observed.

I claim:

1. A new and distinct cultivar of ornamental *Miscanthus sinensis* plant named 'Oktoberfest' as herein described and illustrated, suitable as a potted plant, for the garden, and for cut flower arrangements.

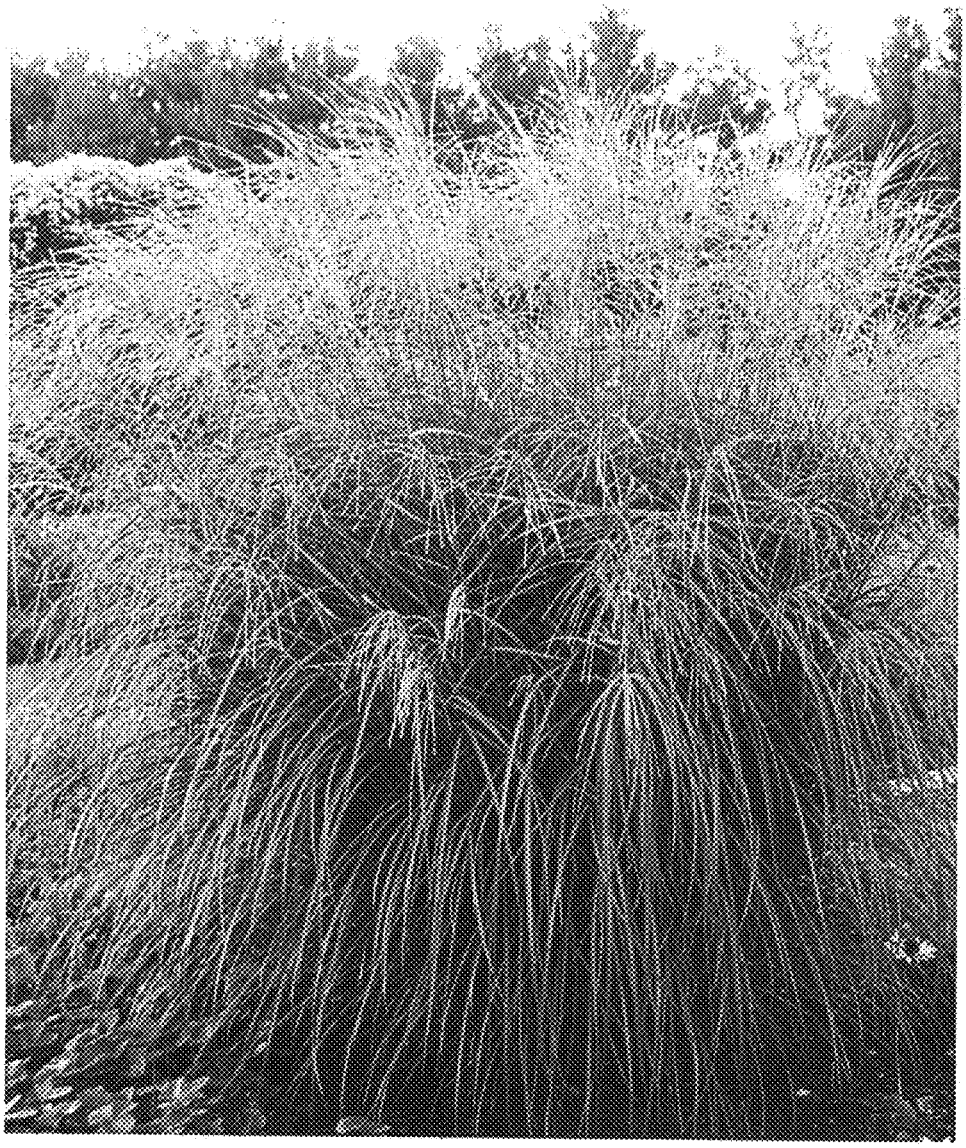

* * * * *